United States Patent
Upadhyay et al.

(12)

(10) Patent No.: US 6,291,483 B1
(45) Date of Patent: *Sep. 18, 2001

(54) METHODS FOR PREVENTION AND TREATMENT OF SEPTIC SHOCK

(75) Inventors: Shakti N. Upadhyay; Suman Dhawan, both of New Delhi (IN)

(73) Assignee: National Institute of Immunology, New Delhi (IN)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/022,299

(22) Filed: Feb. 11, 1998

Related U.S. Application Data

(62) Division of application No. 08/789,464, filed on Jan. 27, 1997.

(30) Foreign Application Priority Data

Feb. 14, 1996 (IN) .......................................... 294/96

(51) Int. Cl.$^7$ .................................................. A61K 31/445
(52) U.S. Cl. .......................................... 514/321; 514/320
(58) Field of Search ............................................ 514/321

(56) References Cited

FOREIGN PATENT DOCUMENTS

316051 * 12/1995 (JP) .

OTHER PUBLICATIONS

Berkow et al., "The Merk Manual of Diagnosis and Therapy, 14th Edition", pp. 54–57, 1982.*
Translation of JP 316051, Dec. 5, 1995.*
Ghosh et al., "Effect of berberine chloride on *Leishmania donovani*", Indian J. Med. Res 78, Sep. 1983, pp. 407–416.*
Heumann et al., "Pathogenesis of Sepsis", Scinetific American, Science & Medicine, Dec. 1994, pp. 2–11.*
Bhakuni, D.S. et al. Ch. 2, Protoberberine Alkaloids for the Alkaloids, vol. 28, 1986 Academic Press p. 95–99.
Sabir, M. et al., Ind. J. Physiol. Pharmacol. 22(1): 9–23, 1978.
Akhter, M.H. Indian J. Med. Res. 65, 1, Jan. 1977, p. 133–141.
Berlin, G. Agents Actions, Apr. 1984 14(3–4) Abstract (401–4).
Berlin, G. Int. Arch. Allergy–Appl. Immunol. 1983, 71(4): Abstract (332–9).
Ghosh, A.K. et al. Ind. J. Med. Res. 78, Sep. 1983, pp. 407–416.
Akhter, M.H. Ind. J. Med. Res. 70, Aug. 1979, p. 233–241.
Krey, A.K. Science vol. 166, Nov. 1969 p. 755–757.
USP Dictionary of Usan and International Drug Names P–89, 1997.

* cited by examiner

*Primary Examiner*—Dwayne C. Jones
(74) *Attorney, Agent, or Firm*—Ladas & Parry

(57) ABSTRACT

Berberine or pharmaceutically acceptable salts thereof either alone or in combination with cyclosporin can be used to treat or prevent graft vs. host disease. Berberine or pharmaceutically acceptable salts thereof can also be used to treat or prevent septic shock syndrome.

21 Claims, 7 Drawing Sheets

METHODS FOR PREVENTION AND TREATMENT OF SEPTIC SHOCK

This application is a Divisional of Ser. No. 08/789,464 filed Jan. 27, 1997.

BACKGROUND OF THE INVENTION

1. Field of the Invention

It is essential for a host that its immune system be responsive to foreign entities especially disease causing pathogens. However, under certain conditions or in specific situations, the immune response may need to be selectively regulated or suppressed. These situations are generally encountered before, during or after organ or bone marrow transplants or to control or treat autoimmune disorders. There are also situations where an uncontrolled immune response triggered by a pathogen or a product could be deleterious for the host, as for example, in the case of septic shock syndrome. The prophylaxis and/or treatment of all such clinical manifestations requires the use of immunosuppressive drugs which can selectively inhibit T cell and/or macrophage responses to specific challenges.

2. Description of the Related Art

In recent years the number of organ transplants including allogenic bone marrow transplants have increased considerably due to their use as a therapeutic option for, inter alia, hematologic, immunologic and malignant disorders. Transplant of bone marrow has led to an immunological complication known as Graft-vs-Host disease (GVHD), where immunologically competent cells of the graft cause damage to the recipient host. This effect is primarily mediated by T lymphocytes (Grebe and Streilein, 1976). Basically, the Major Histocompatibility Complex (MHC) antigens present on all tissue provide the immunological identity to an individual which helps the immune system distinguish between self and non-self so that the immune system can destroy foreign invaders while preserving normal healthy tissue. When MHC bearing tissue is transferred from one individual to another via for example, an organ transplant, it is recognized by the T cell of the recipient as foreign which leads to rejection of tissue in a Host-vs.-Graft (HVG) reaction. However, when MHC bearing immunocompetent cells are transferred from a normal individual to an immunocompromised host (e.g. bone marrow transplant), the grafted immunocompetent cells (mainly T lymphocytes) recognize the differences in host MHC complex and initiate a Graft-vs.-Host reaction leading to GVHD. GVHD is an immunopathophysiologic process with two consecutive phases: the afferent phase, where the recipient tissue first activates the T lymphocytes from the donor and in the second phase (i.e. the effector phase), activated donor cells then secrete inflammatory cytokines, including IL-2 (interleukin 2), IFN-g (interferon g) and TNF-a (tumor necrosing factor a) and recruit additional cells and focus attack on recipient targets. The main targets include the skin, gastrointestinal tract, liver and lymphoid organs (Ferrara and Deeg, 1991). Acute GVHD occurs in approximately 50% of patients who receive bone marrow transplants and is a primary or contributory cause of death in 15–45% of the 50% of the patients who develop GVHD after bone marrow transplant. The post-transplant period is also associated with immune dysfunction due to use of prior ablative radio/chemo therapy to suppress the recipient's lymphoid system (especially mature T lymphocytes) and to allow engraftment of a donor organ (e.g. bone marrow). This in turn often results in severe infections, which are also a major cause of morbidity and mortality in transplant patients. Therapeutic strategy in such situations requires a selective suppression of alloreactivity of T cells and protection against opportunistic infections.

MACROPHAGE RESPONSE TO ENDOTOXINS

While macrophages play an important role in elimination of microbial infections, their response to microbial products (endotoxins) could lead to a pathological situation known as septic shock syndrome (Lynn and Golenbock 1992). Ironically, the same mediators and effector molecules which are involved in microbiocidal activity of macrophages, if produced in excess, lead to septic shock. Endotoxins, lipopolysaccharides (LPS) released by disintegrating bacteria activate macrophages to produce tumor necrosis factor (TNF-a), which in turn initiates a cascade of inflammatory reactions including activation of the complement system, enhanced expression of adhesion molecules on the endothelial lining of the blood vessels, activation of neutrophils and production of reactive oxygen intermediates (ROI) (Galanos and Freudenberg, 1993). Activation of complement results in the release of factors which act as chemotactic and activation signals for neutrophils. Expression of adhesion molecules causes adherence of neutrophils to the endothelial lining of blood capillaries. These changes lead to extravasation of activated neutrophils and tissue damage due to release of ROIs. Widespread tissue damage ultimately results in multiorgan dysfunction and septic shock. Therapeutic strategy under such circumstances requires reduction of production of TNF-a by macrophages in response to microbial endotoxin or suppression of TNF-a induced effects on the target cells.

Strategies for immunosuppressive therapy are generally aimed at interfering with different stages of T cell activation. Extensive work has been carried out to identify new immunosuppressive drugs which can selectively block T cell activation. However. currently available immunosuppressive therapies are inadequate because they exhibit limited efficacy, modest selectivity, considerable toxicity and are generally very costly.

A) GRAFT-VS-HOST DISEASE (or rejection of organ transplant):

Methotrexate has been widely used for prophylaxis of GVHD in humans (Thomas et al. 1975), although its efficacy is still controversial. The most commonly used drug of choice has been cyclosporin (Tutschka et al. 1979; Powels et al. 1980). However, a review by the International Bone Marrow Transplant Registry failed to indicate a benefit of cyclosporin over methotrexate (Bortin, 1985). Alternative approaches to prevent GVHD include treatment of donor bone marrow in vitro with antithymocyte globulin, monoclonal antibodies or lectins to deplete T lymphocyctes.

Treatment of established acute GVHD has been unsatisfactory. A variety of agents including corticosteroids, antithymocyte globulin, cyclosporin, and azathioprine have been used without convincing evidence of improvement in survival (Doney et al. 1981; Kendra et al., 1981; Kersey et al., 1983; Sullivan 1983; Kennedy et al. 1985). The problem is that the approaches used to treat GVHD further exacerbate the severe immune suppression making the host vulnerable to opportunistic infections leading to a decrease in survival.

Other immunosuppressive agents that are currently undergoing clinical trials include, FK-506, rapamycin, RS-61443, mizoribine, deoxyspergualin and brequinar sodium, etc. FK-506, like cyclosporin, is derived from fungal sources. The immunosuppressive effects of both cyclosporin and FK-506 block early events of T cell activation via similar mechanisms. They act by forming a heterodimeric complex with their respective cytoplasmic receptor proteins (i.e. cyclophilin and FK-binding protein) which inhibit phosphatase activity of calcinurin thereby inhibiting expression of nuclear regulatory proteins and T-cell activation genes (Schreiber, 1992). Corticosteroids are known to be immunosuppressive and are used for a variety of inflammatory diseases. These steroids inhibit T cell proliferation, T cell dependent immunity and cytokine gene expression (Knudsen et al., 1987, Zanker et al., 1990, Arya et al., 1984). The anti-metabolite azothioprine is a thioguanine derivative of 6-mercaptopurine (Elion, 1967) and it acts as a purine antagonist and functions as an anti-proliferative agent. Rapamycin is also a macrolide like FK-506, but it inhibits T cell response to IL-2 rather than signal transduction for T cell activation (Morris, 1992). RS-61443, the semi-synthetic derivative of the fungal antibiotic, mycophenolic acid, has been found to inhibit allograft rejection in experimental animals (Morris and Wang, 1991). Mizoribine, a imidazole nucleoside, blocks the purine biosynthetic pathway and inhibits mitogen stimulated T- and B-cell proliferation in a similar manner to azathioprine and RS-614443 (Turka et al. 1991). Deoxyspergualin, a synthetic analog of spergualin, has been found to exert immunosuppressive properties in pre-clinical transplantation models (Takeuchi et al., 1981; Umeda et al., 1985). The anti-metabolite brequinar sodium is an inhibitor of dihydro-orotate dehydrogenase and blocks formation of the nucleotides uridine and cytidine via inhibition of pyrimidine synthesis. However, many of these drugs are associated with toxic effects like gastrointestinal complications, hypertrophic gums, nephrotoxicity, hypertension and myelo-or hepatotoxicity.

B) Endotoxin-induced Septic Shock

At present, there is no effective therapy to prevent septic shock. Antibiotics which are otherwise effective in inhibiting microbial growth do not protect against septic shock since it is the endotoxin released by disintegrating dead bacteria that induces macrophages to produce TNF-a. Various therapeutic approaches which are undergoing clinical trials (for review, see Glauser et al., 1994) include antibodies directed against endotoxin, LPS (Greenman et al., 1991; Ziegler et al., 1991) or TNF (Cross, 1993) and antagonists to IL-1 receptor (Fisher et al., 1993) or platelet activating factor (Dhainaut et al., 1993). Experimental studies have shown bactericidal/permeability protein (BPI) produced by neutrophils antagonizes LPS and appears to have therapeutic potential (Marra et al., 1990; Weiss et al., 1992). Soluble TNF-a receptor (Lesslauer et al., 1991) and IL-10 (Howard et al., 1993; Gerard et al., 1993) have also been found to protect experimental animals from lethal endotoxemia. Microbial products such as glucan have experimentally been shown to enhance host resistance to septic shock (Lahnborg et al., 1982).

C) Berberine:

The present invention describes a new method of immunosuppressive therapy utilizing a protoberberine alkaloid, Berberine or its pharmaceutically acceptable salts. Berberine may be isolated from *Berberis aristata*. This plant has been widely used in traditional Indian medicine for treatment of gastroenteritis, and skin and eye infections (Chopra et al., 1956; Nadkarni 1954). The chemistry and pharmacological effects of protoberberine alkaloids have been described in the scientific literature. Berberine has been reported to have direct anti-bacterial (Sado, 1947; Dutta and Panse, 1962), anti-amoebic (Subbaihah and Amin, 1967; Dutta and Iyer, 1968) and anti-leishmanial effects (Dasgupta and Dikshit, 1929; Steck, 1974; Ghosh et al., 1983, 1985) and cytotoxic effects against certain types of tumor cells (for review see Bhakuni and Jain 1986). Berberine has been shown to complex with DNA (Krey and Hahn 1969; Maitia and Chowdhuri, 1981) and is being used as a specific stain for mast cells because of its specificity of binding with heparin (Berlin and Enerback, 1983, 1984).

Japanese patent 07-316051 published Dec. 5, 1995 (Kangegafuchi Chemical Co. Ltd.) discusses the use of berberine or its pharmacologically tolerable salt as an immunosuppressant specifically for autoimmune diseases such as rheumatism and for treatment of allergies and to prevent rejection of isografts. This reference discloses that berberine inhibits antibody production by B cells, suppresses humoral immunity and has no effect on propagation of T cells.

SUMMARY OF THE INVENTION

The present invention provides a new immunosuppressive therapy which selectively suppresses the specific allogenic response of immunocompetent cells as to control graft-vs-host reaction. The present invention also provides a way to protect an immunocompromised host against septic shock caused by opportunistic infections. A further aspect of this invention is that administration of berberine or its pharmaceutically acceptable salts is effective to prevent septic shock in individuals who are not immunocompromised. It has also been found that administration of berberine or its pharmaceutically acceptable salts and cyclosporin results in superior results when compared to use of the active agents berberine or its pharmaceutically acceptable salts alone or cyclosporin alone.

An object of this invention is to administer berberine or its pharmaceutically acceptable salts alone or in combination with cyclosporin to prevent or treat graft vs. host reaction.

A further object of this invention is to administer berberine or its pharmaceutically acceptable salts to prevent or treat septic shock.

One object of this invention is to administer berberine or its pharmaceutically acceptable salts to inhibit the response of T cell lymphocytes against allogenic or antigenic stimulus.

A still further object of this invention is to administer berberine or its pharmaceutically acceptable salts to inhibit T cell activation.

Another object of the invention is to administer berberine or its pharmaceutically acceptable salts to block T cell activation.

Yet another object of the invention, is to suppress TNF-a induced effects on the target cells.

DETAILED DESCRIPTION OF THE INVENTION

Figure 1:
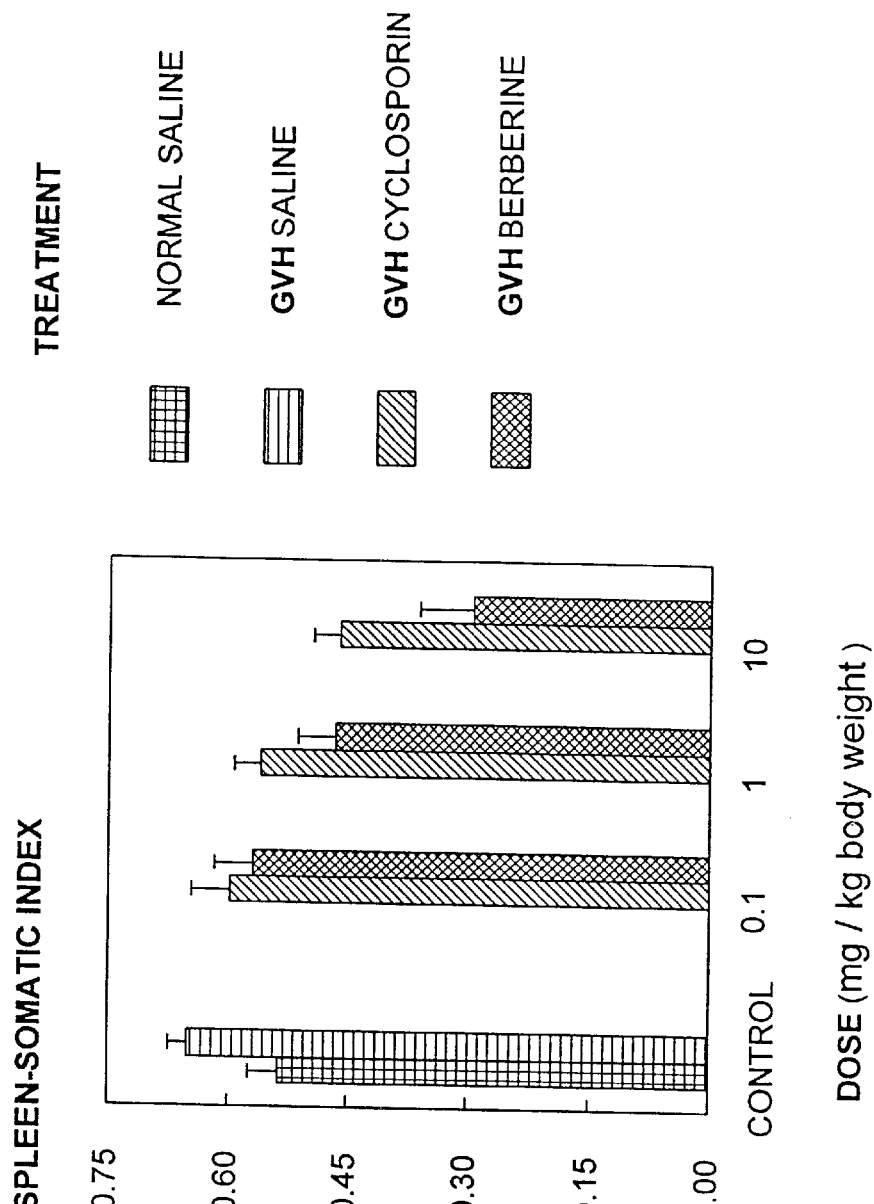
FIG. 1 shows the effect of cyclosporin and Berberine sulphate on graft-vs-host reaction.

The present invention provides a new immunosuppressive therapy comprising use of a protoberberine alkaloid, berberine or its pharmaceutically acceptable salts. Berberine is isolated from a medicinal plant, *Berberis aristata* and is also commercially available. Berberine and its pharmaceutically acceptable salts can also be produced synthetically (Kametani 1969 and Sainsburg 1969). Another aspect of the invention is an improved immunosuppressive therapy comprising use of berberine or its pharmaceutically acceptable salts and cyclosporin.

The method of treatment of this invention induces selective immunosuppression by functionally inhibiting the response of T lymphocyctes against allogenic or antigenic stimulus and also suppresses the inflammatory response of macrophages to bacterial endotoxin. The present method, therefore, can be used in clinical situations, such as, where a patient is immunocompromised, for example, prior to and/or following bone marrow transplant. The present method can also be used in patients who will undergo organ transplant or who have undergone an organ transplant. The present method can also be used for a patient with an autoimmune disorder especially T cell mediated autoimmune disorders. In the method according to this invention, T lymphocyte activation and/or proliferation is inhibited. It is expected that when berberine or its pharmaceutically acceptable salts is administered according to the method of this invention, IL-2 induced T cell proliferation is inhibited and $IFN_\gamma$ production by T cells following mitogenic, allogenic or antigenic challenge is also inhibited.

The method of the invention can also be used to treat IL-2 and/or $IFN_\gamma$ mediated autoimmune disorders. The method of this invention can also inhibit TNF mediated pathology in TNF-a sensitive target tissue.

According to another aspect of this invention berberine or its pharmaceutically acceptable salts can be administered to treat or prevent septic shock in immunocompromised or non immunocompromised patients. Berberine or its pharmaceutically acceptable salts can also be used to treat or prevent TNF-a induced septic shock.

The present method of treatment, as described herein appears to be more potent and less toxic than treatment with the known immunosuppressive drugs.

Berberine and its pharmaceutically acceptable salts are commercially available. Berberine may also be extracted and isolated from *Berberis aristata*, a plant belonging to family Berberidaceae. One method of extracting and isolating berberine from *Berberis aristata* comprises coarsely grinding the air dried stems/roots of *Berberis aristata* and subjecting this material to thorough defatting with non-polar solvents like hexane or petroleum ether at 60–80° C. followed by extraction with 95% ethanol or 95% methanol in water. The alcoholic extract is then concentrated in a water bath and the basic constituents are extracted from the residue preferentially with a 7% aqueous solution of citric acid or acetic acid or dilute $HCl/H_2SO_4$. The aqueous acidic solution was treated with Mayer's reagent and filtered. The Mayer's complex (precipitate) so obtained was either directly loaded on a column of Amberlite-IRA 400 (Cl—) (Amberlite is a packing made from asbestos with binders. IRA-400 is an indicator of mesh size and grade equivalent to 20–50 mesh strongly cationic resin) and eluted with methanol, or stirred with Amberlite-IRA 400 (Cl—) and the alkaloid chloride was then filtered from resin, lyophilized, adsorbed on silica gel and eluted on a column of silica with chloroform ($CHCl_3$):methanol (MeOH) (increasing polarity). $CHCl_3$:MeOH (90:10) elutes resulted in a biologically active compound. The compound, appearing as yellowish needles, m.p. 145–147° C., thus obtained was found to be soluble in ethanol, methanol, water and insoluble in chloroform, benzene and petroleum ether at 60–80° C. It did not give any test for phenols. The C.I. Mass spectrum of the compound gave MH+ at m/z 337, revealing its molecular weight to be 336. This fact, coupled with the elemental analysis data gave the molecular formula of the compound to be $C_{20}H_{18}NO_4$. The U.V. spectrum of the compound showed absorption maxima at 263 and 345 (log e 4.4 & 4.4) and minima at 250, 305 and 370 nm (log e 4.1, 3.8 and 3.7), the spectral pattern remaining unaffected by addition of an acid. Upon addition of sodium borohydride the compound was decolorized and a distinct shift in its UV pattern was observed, thus showing the native compound to be a quaternary alkaloid in nature. The UV absorption minimum at 305 nm is typical of 2,3,9,10 oxygenated protoberberine alkaloids (Shamma, 1972). On the basis of this data the compound was identified to be berberine and it was further confirmed by a direct comparison with an authentic sample of berberine (m.m.p., Co-TLC an Co-IR). The chemical structure of berberine is given below:

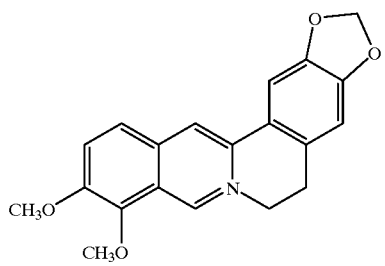

To prevent GVHD and septic shock in patients who will undergo bone marrow or organ transplants, in cases where it is possible, suitable protocols for administration of berberine or its pharmaceutically acceptable salts include administration of berberine or pharmaceutically acceptable salts to the patient who will receive the transplant prior to the transplant. It is preferred that the berberine or its pharmaceutically acceptable salts be administered to the patient at least seven days prior to receiving the transplant. In another embodiment, berberine or its pharmaceutically acceptable salts can be administered to the patient about 24 hours before the bone marrow or organ transplant and continued thereafter. Berberine or its pharmaceutically acceptable salts can also be administered to the patient daily following the transplant or both prior to and after the transplant takes place. Following the transplant, Berberine or its pharmaceutically acceptable salts can be administered for about two weeks up to several months depending on the clinical condition and progress of the patient. It is preferred that berberine or its pharmaceutically acceptable salts be administered immediately after the transplant to protect against bone marrow rejection or organ graft rejection and to protect against the development of septic shock syndrome. In another embodiment of the invention berberine or its pharmaceutically acceptable salts is administered to the organ or marrow donor for at least seven days before the organ or marrow is removed from the donor.

Berberine or its pharmaceutically acceptable salts can also be administered to immunocomprised or immunocompetent patients to treat or prevent septic shock. Berberine or its pharmaceutically salts can also be administered to patients, (either immunocompromised or nonimmunocompromised) suffering from septic shock. Berberine or its pharmaceutically acceptable salts can be administered to patients who have or who will undergo surgery to prevent septic shock. It is preferred that berberine or its pharmaceutically acceptable salts be administered at least 24 hours before the surgery. Berberine or its pharmaceutically acceptable salts can also be administered to patients who have been burned to prevent or treat septic shock. It is preferred that pharmaceutically acceptable salts of berberine be used in the method of this invention. It is more preferred that the salts are berberine sulphate or berberine chloride.

Berberine or its pharmaceutically acceptable salts may be administered via any appropriate dosage routes, specifically, topically, orally, by injection, transdermally, intravenously, intraarterially, intraperitoneally, intrapleurally, subcutaneously, intramuscularly, sublingually, intraepidermally or rectally. The preferred routes of administration are intravenously, intraarterially, orally or topically, Topical preparations include but are not limited to ointments, gels, salves, creams, lotions and sprays. Berberine and its pharmaceutically salts can also be administered in the forms of tablets, granules, powder, capsules, caplets and the like. Berberine salts are water soluble and can be administered in water. Berberine and its pharmaceutically acceptable salts can also be administered in other pharmaceutically acceptable carriers, diluents, solvents and excipients. The daily dose of berberine or its pharmaceutically acceptable salts is in the range of 1 to 20 mg/kg of body weight; preferably 5 to 10 mg/kg of body weight. It is more preferred that the dosage be 10 mg/kg of body weight. The daily dose of berberine or its pharmaceutically acceptable salts can be administered as a single dose or in multiple doses. The same protocol can be used for administration of berberine or its pharmaceutically acceptable salts to organ or marrow donors.

In another aspect of this invention it has also been found that administration of berberine or its pharmaceutically acceptable salts in combination with cyclosporin results in a superior and/or synergistic effect of inhibiting graft vs. host reaction. It is preferred that the drugs be administered together or immediately following one another. If the drugs are not administered together, cyclosporin can be administered and then berberine or its pharmaceutically acceptable salts or vice versa.

The amount of cyclosporin administered can be in the range of 0.1 mg/kg to 15 mg/kg of body weight. It is preferred that the amount of cyclosporin be 1 mg/kg to 10 mg/kg of body weight. It is more preferred that the amount be 10 mg/kg of body weight. The amount of berberine or its pharmaceutically acceptable salts that can be administered is in the range of 1 mg/kg to 15 mg/kg of body weight. It is more preferred that the amount of berberine or its pharmaceutically acceptable salts be in the range of 5 to 10 mg/kg of body weight. It is more preferred that the amount be 10 mg/kg of body weight. The mode of administration and pharmaceutical forms of berberine and its pharmaceutically acceptable salts and cyclosporin are the same as described above for berberine and its pharmaceutically acceptable salts.

Mice models for GVH and endotoxin-shock were used to illustrate the present invention. The mice models are experimental models for clinical situations. The invention described above is further illustrated by the following experimental studies and such experiments should not be construed as limiting the objectives and the scope of the invention.

EXAMPLE-1

F-1 hybrid of BALB/c-DBA/2J (both $H-2^d$ haplotype) mice were used as recipient of splenocytes from one of the parental strains (semi-syngenic transplant). The splenocytes were grafted intra-peritoneally or intra-venously in F-1 mice on day-0. Graft recipients were divided into experimental and control groups. Each experimental and control group contained a minimum of 6 mice. Experimental groups were injected intra-peritoneally daily from day 1–7, with berberine sulphate at dosages ranging from 0.1 mg/kg to 10 mg/kg of body weight or cyclosporin (for comparison) at a dose range of 0.1 mg/kg to 10 mg/kg body weight of the animal; the control group was treated with saline. Animals were sacrificed on day-8 and spleen and body weights were recorded. The treatment with the berberine sulphate (10 mg/kg) showed significant inhibition of GVH reaction in comparison to the control and appeared more potent than cyclosporin as indicated by the splenomegaly index (FIG. 1).

EXAMPLE-2

Figure 2:
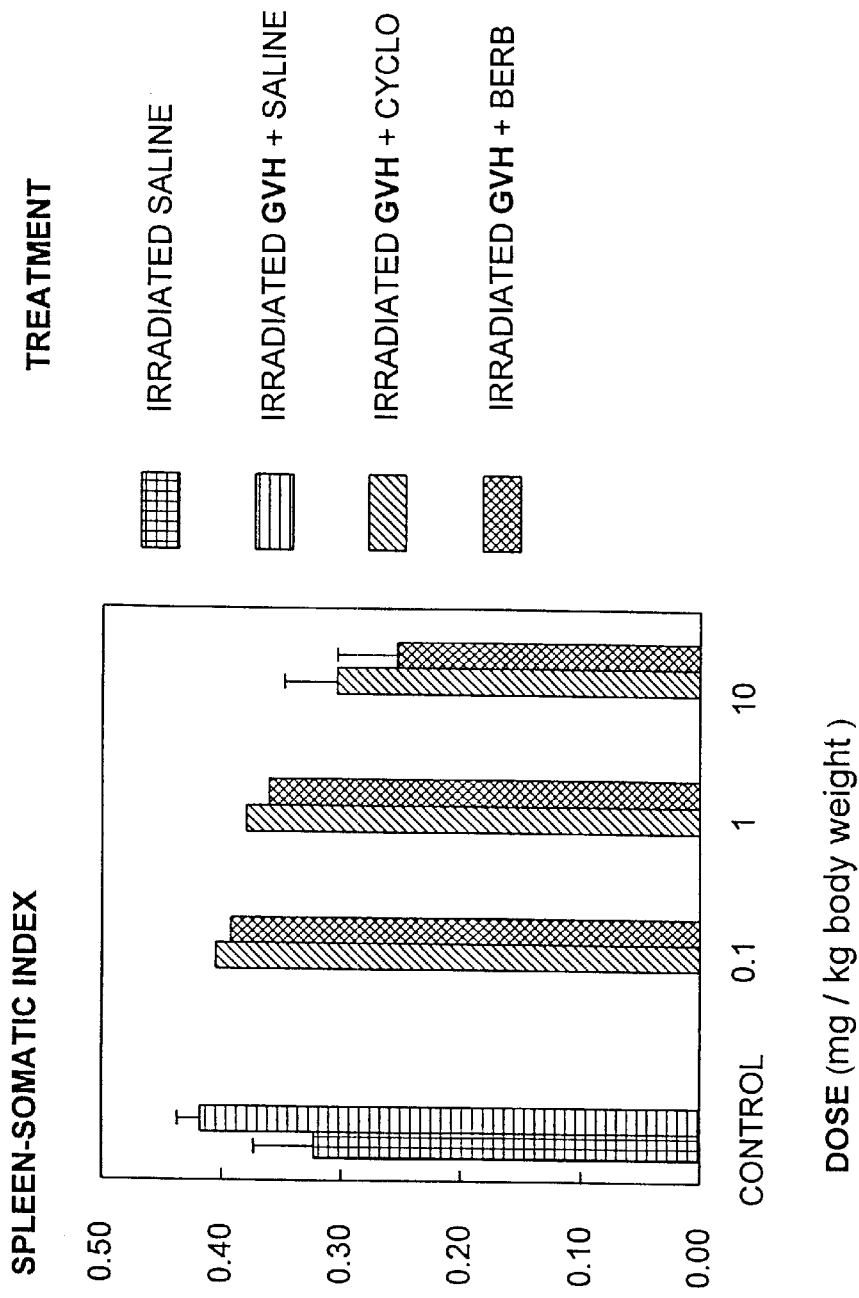
FIG. 2 shows the effect of Berberine sulphate on graft-vs-host reaction.

BALB/c inbred mice were given sub-lethal irradiation (450 rads) and were grafted (i.p. or i.v. route) with allogenic splenocytes from DBA/2J inbred mice on day-0. Graft-recipient animals were divided into experimental and control groups. Each experimental and control group contained a minimum of 6 mice. Experimental groups were injected intra-peritoneally daily from day 1–7, with berberine sulphate at a dose range of 0.1–10 mg/kg of body weight of the animal or injected intra-peritoneally daily from day 1–7 with cyclosporin at a dose range of 0.1 to 10 mg/kg of body weight; the control group was treated with saline. Animals were sacrificed on day-8 and spleen and body weights were recorded. The treatment with berberine sulphate (10 mg/kg) showed significant inhibition of GVH in comparison to control appeared more potent than cyclosporin as indicated by the splenomegaly index (FIG. 2).

EXAMPLE-3

Figure 3:
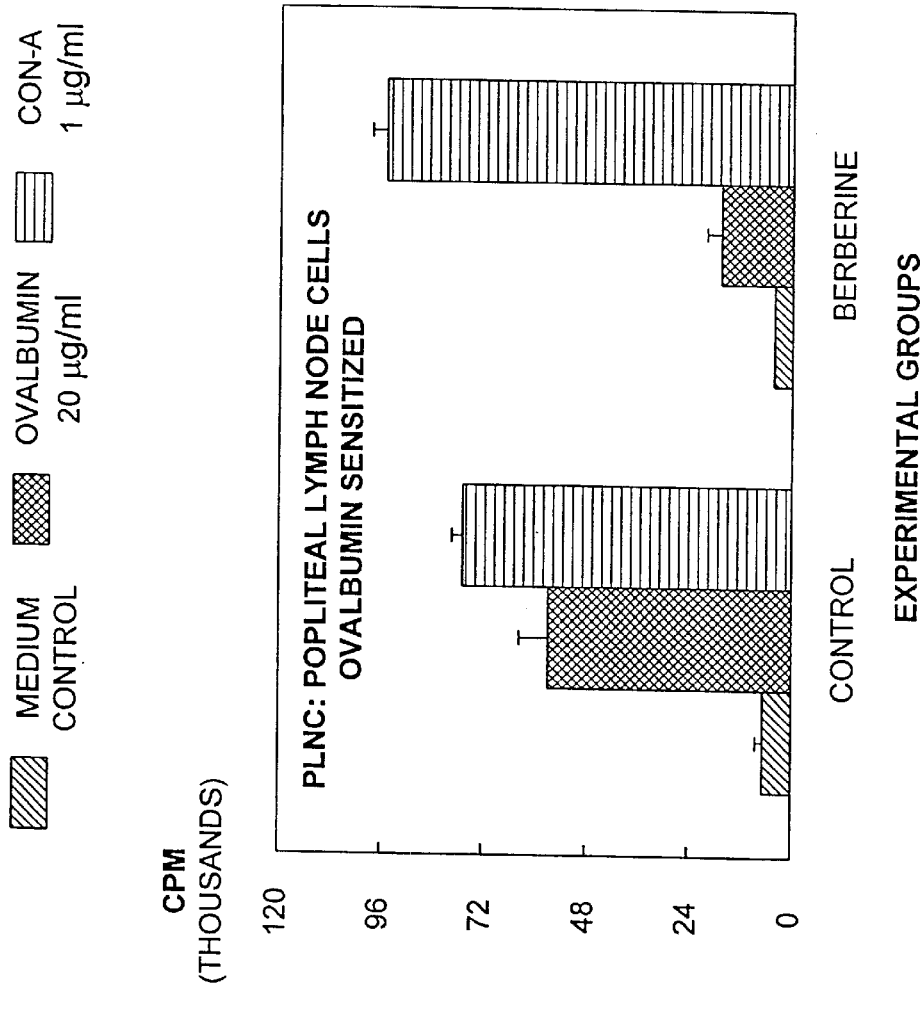
FIG. 3 shows the effect of Berberine sulphate on antigen specific and mitogenic response of popliteal lymph node cells.

Normal BALB/c inbred mice were sensitized to ovalbumin by a single footpad immunization with complete Freund's adjuvant on day-0 and were divided into experimental and control groups. Each experimental and control group contained a minimum of 6 mice. Experimental groups were injected intra-peritoneally daily from day 1–7, with berberine sulphate at a dose range of 10 mg–0 mg/body weight of the animal; the control group was injected with saline. On day-8, popliteal lymph node cells (PLNC) were isolated and challenged in vitro with ovalbumin or T cell mitogen, Con-A. While the pLNC from saline treated mice showed normal mitogenic and antigen recall response, those from berberine sulphate treated mice showed significant suppression of antigenic response to ovalbumin while maintaining normal mitogenic response to Con-A. (FIG. 3).

The results obtained indicate that berberine inhibits T cell activation in response to specific antigenic challenge by blocking certain signal transduction steps that are not involved in Con-A induced T cell activation and proliferation. Although, the exact mechanism of action of berberine remains to be elucidated, the mechanism may be inhibiting co-stimulatory signal transduction pathways necessary for allogenic/antigenic induced T cell activation and proliferation.

EXAMPLE-4

Figure 4:
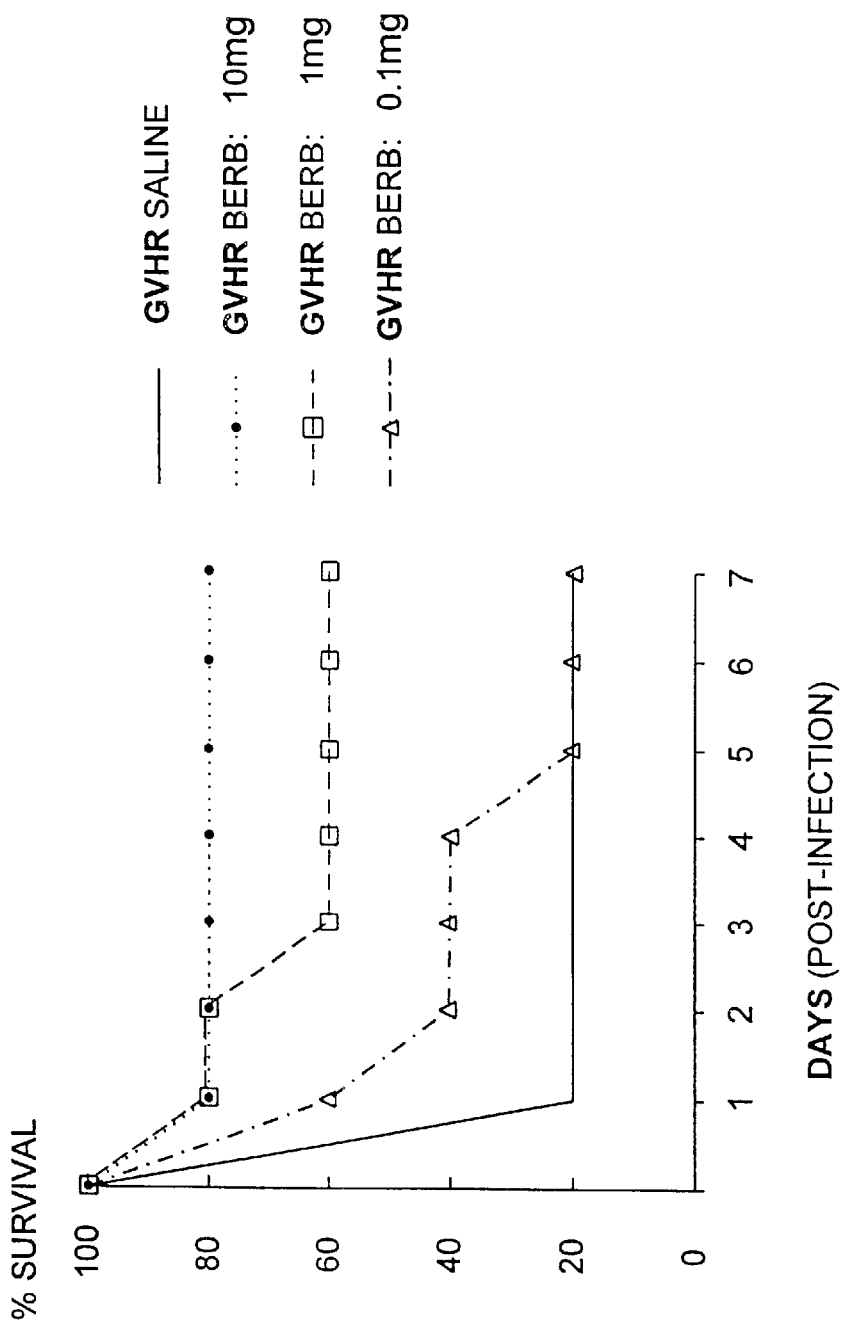
FIG. 4 shows the effect of Berberine sulphate against *E. coli* induced septic shock in mice undergoing GVHR.

F-1 hybrid of BALB/c-DBA/2J mice were used as recipient of splenocytes from one of the parental strain (semi-syngenic transplant). The splenocytes were grated intra-peritoneally or intra-venously in F-1 mice on day 0. Graft-recipient animals were divided into experimental and control groups. Each experimental and control group contained a minimum of 6 mice. Experimental groups were injected intra-peritoneally, daily from day 1–7, with berberine sulphate at a dose range of 10 mg–0.1 mg/kg body weight of the animal; control group was treated with saline. On day-8, all the groups were given a lethal dose of pathogenic strain of *escherichia coli* or bacterial endotoxin, lipopolysaccharide (LPS), intra-peritoneally. While all animals in control group died within 24 hours, 80% of the animals treated with berberine sulphate (10 mg/kg) survived (FIG. 4).

EXAMPLE-5

Figure 5:
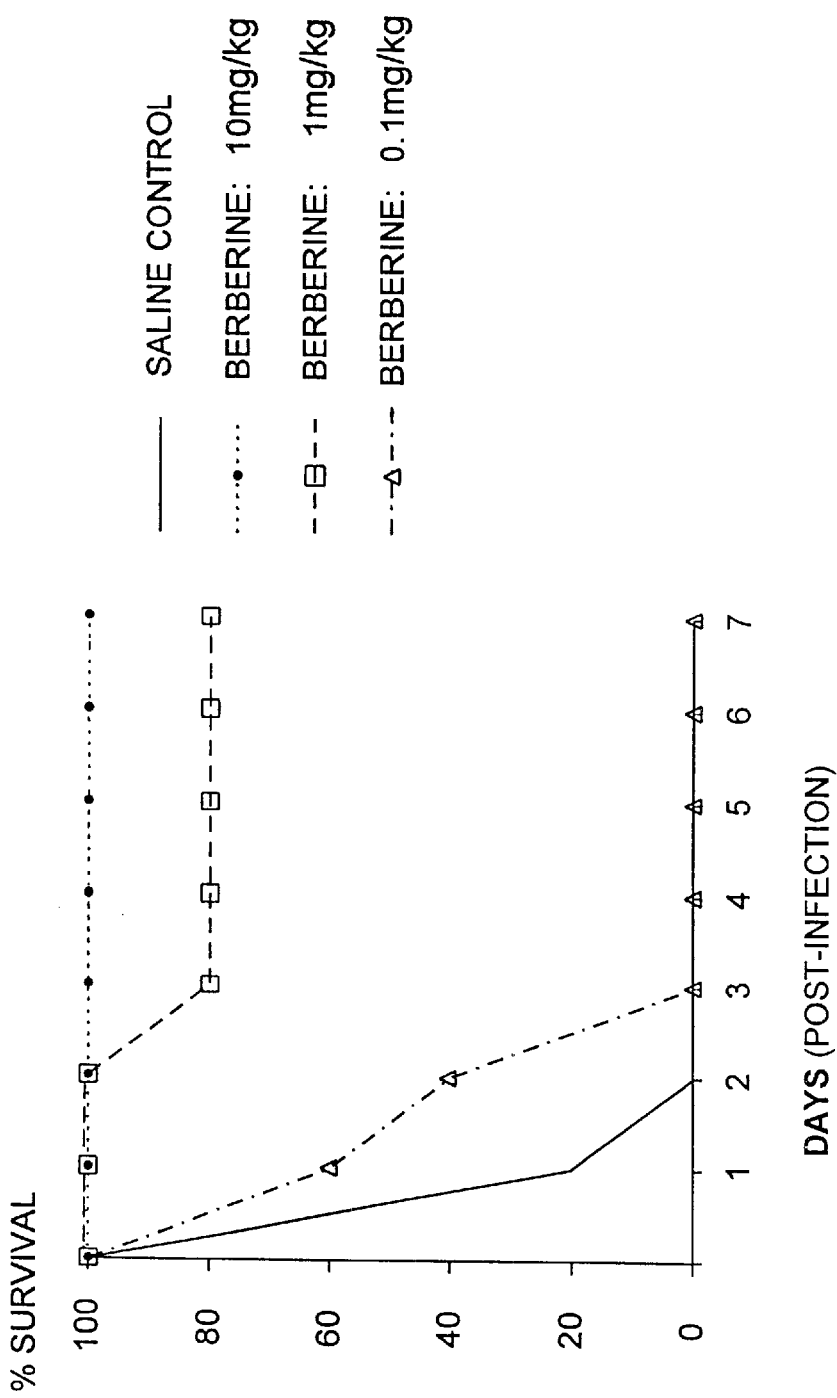
FIG. 5 shows the immunoprotective effect of Berberine sulphate against lethal *E. coli* infection in BALB/C mice.

Normal BALB/c inbred mice were injected intraperitoneally daily, for 7 days, with berberine sulphate at a dose range of 10mg–0.1 mg/kg body weight of the animal; untreated animals injected with saline were kept as control. Each experimental and control group contained a minimum of 6 mice. On day 8, all the groups were given a lethal dose of pathogenic strain of *Escherichia coli* or bacterial endotoxin, lipopolysaccharide (LPS), intra-peritoneally. While all animals in the control group died within 24–48 hours of infection, all animals treated with berberine sulphate(10 mg/kg) survived (FIG. 5).

EXAMPLE-6

Figure 6:
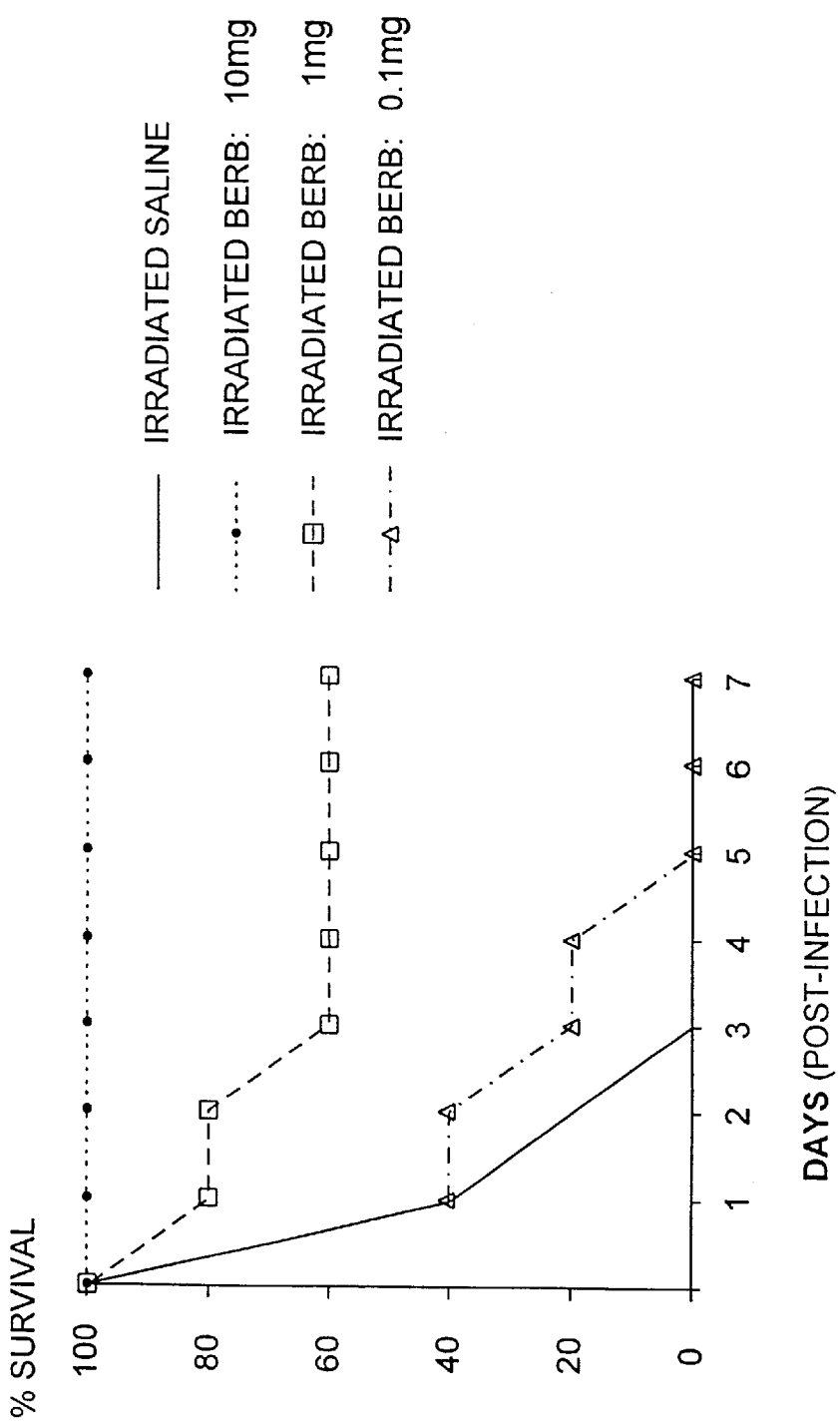
FIG. 6 shows the immunoprotective effect of Berberine sulphate against sub-lethal infection in irradiated mice.

Normal BALB/c inbred mice were given a single sub-lethal irradiation (450 rads) on day-0, to render these animals immunocompromised, and divided into experimental and control groups. Each experimental and control group contained a minimum of 6 mice. Experimental groups were injected intra-peritoneally, daily from day 1–7, with berberine sulphate at a dose range of 10 mg–0.1 mg/kg body weight of the animal; control group was treated with saline. On day-8, all the groups were given a lethal dose of pathogenic strain of *Escherichia coli* or bacterial endotoxin, lipopolysaccharide (LPS), intra-peritoneally. While all animals in the control group died within 24–48 hours of infection, all animals treated with berberine sulphate(10 mg/kg) survived (FIG. 6).

EXAMPLE-7

Figure 7:
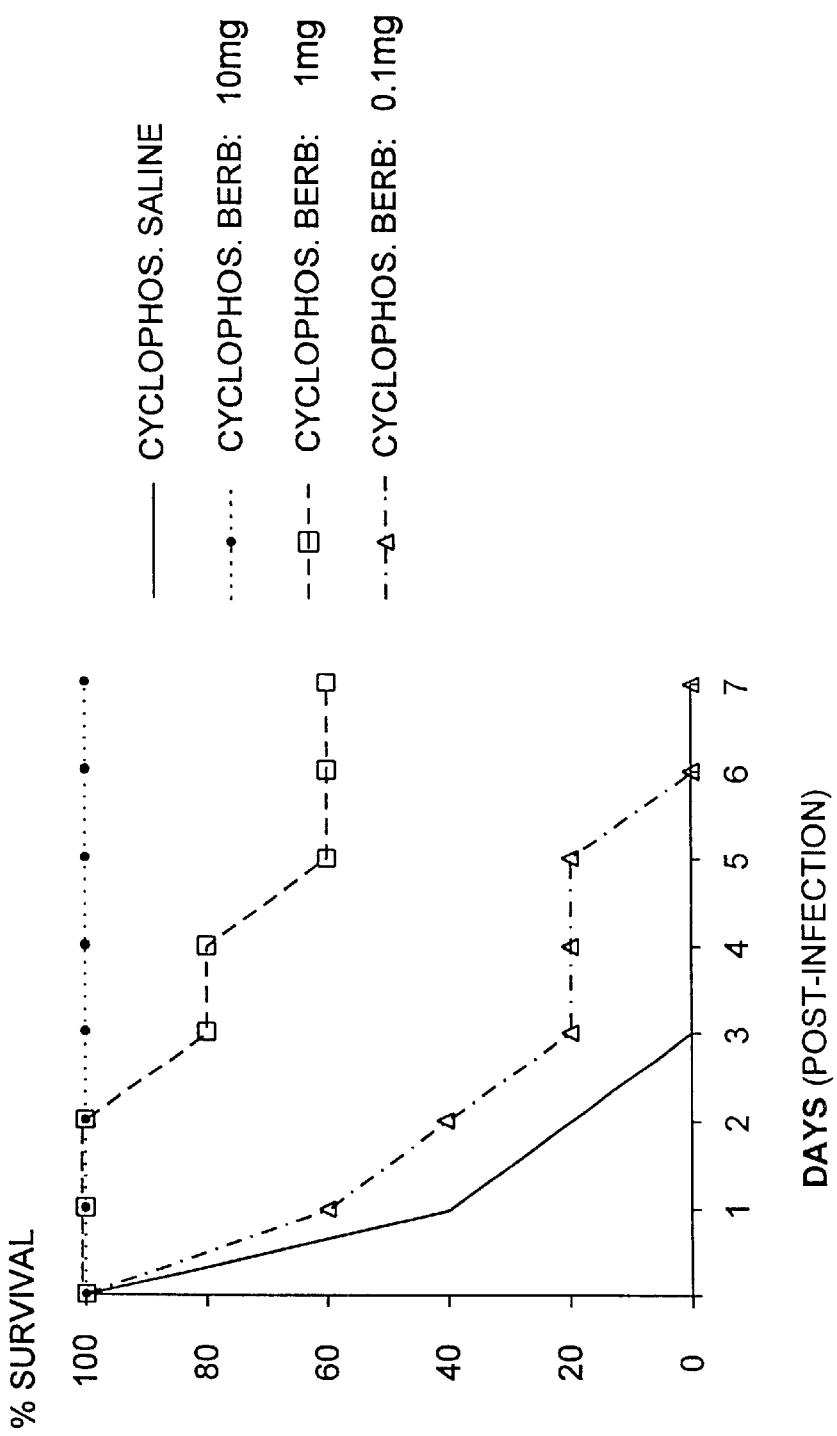
FIG. 7 shows the immunoprotective effect of Berberine sulphate against sub-lethal infection in CY-treated mice.

Normal BALB/c inbred mice were given a single injection of cyclophosphamide (200 ug/animal) on day-0, to render these animals immunocompromised, and divided into experimental and control groups. Each experimental and control group contained a minimum of 6 mice. Experimental groups were injected intra-peritoneally daily from day 1–7 with berberine sulphate at a dose range of 10 mg–0mg/kg body weight of the animal; control group was treated with saline. On day-8, all the groups were given a lethal dose of pathogenic strain of *Escherichia coli* or bacterial endotoxin, lipopolysaccharide (LPS), intra-peritoneally. While all animals in the control group died within 24–48 hours of infection, all animals treated with berberine sulphate (10 mg/kg) survived (FIG. 7).

EXAMPLE-8

Synergistic Effect of Berberine and Cyclosporin

BALB/c inbred mice were given sub-lethal irradiation (450 rads) and were grafted with allogenic splenocytes from DBA/2J inbred mice on day-0, to induce graft-vs-host reaction (GVHR). Animals were divided into different groups and were injected intra-peritoneally with cyclosporin and berberine sulphate alone and different dose combinations (Cyclosporin 0.1–10 mg/kg:Berberine sulphate 0.1–10 mg/kg), daily from day 1–7. Each experimental and control group contained a minimum of 6 mice.

Animals were sacrificed on day-8 and splenocytes were isolated and cultured in vitro for 48 hours and then pulsed with $^3$H-thymidine for 6 hours. Lymphocyte proliferation, indicating degree of GVHR, was measured by counting $^3$H-thymidine incorporation.

Results showed that the treatment with a combination of Cyclosporin:Berberine in the dose ratio of 10:10 mg/kg showed maximum inhibition of GVHR in a synergistic manner (Table 1), bringing the values close to that of non-GVHR control.

TABLE 1

| GROUP | EXPERIMENT (Day - 0) | TREATMENT (Day 1–7) Cyclosporin/Berberine (0.1–10 mg/kg) | SPLENOCYTE PROLIFERATION (CPM) |
|---|---|---|---|
| Group 1: | Irradiated control | Saline | 7085 |
| Group 2: | Irradiated-GVHR | Saline | 44,921 |
| Group 3: | Irradiated-GVHR | Cyclosporin(10 mg/kg) | 33,467 |
| Group 4: | Irradiated-GVHR | Berberine (10 mg/kg) | 29,000 |
| Group 5: | Irradiated-GVHR | Cyclosporin (10 mg/kg)* + Berberine (10 mg/kg)* | 6189 |
| Group 6: | Irradiated-GVHR | Cyclosporin (1 mg/kg) + Berberine (10 mg/kg) | 17548 |
| Group 7: | Irradiated-GVHR | Cyclosporin (0.1 mg/kg) + Berberine (10 mg/kg) | 25596 |

*Optimum dose

REFERENCES

Arya S k, Wong-Staal F, Gallo R C: J. *Immunol.*, 133: 273–276, 1984

Berlin G. Enerback L: *Int. Arch. Allergy Appl. Immunol.*, 71, 332, 1983

Berlin G. Enerback L. *Agents Actions*, 14, 401, 1984

Bhakuni, Jain, *Protoberberin Alkaloids, In: The Alkaloids*, Vol. 28: 95–181, 1986, Academic Press, New York Bortin M M: *Exp. Hematol.* 13: 406, 1985

Chopra R N, Nayar S L, Chopra I C: In: *Glossary of Indian Medicinal Plants, Council of Scientific and Industrial Research*, New Delhi, pp, 36, 1956

Cross A S: *Endotoxin News Letter*, 3: 2, 1993

Dasgupta B M, Dikshit B B: *Indian Med. Gaz* 64, 67, 1929

Dhainaut J F, Tenaillon A, Letzulo Y, et al.: *Circ. Shock*, 1: 42, 1993

Doney K C, Weiden P L, Strob R, Thomas E D: *Am. J. Hematol.*, 11: 1, 1981

Dutta N K, Iyer S N: *J Indian Med. Assoc*, 16, 349, 1968

Dutta N K, Panse M V: *Indian J. Med. Res*. 50: 732, 1962

Elion G B: *Fed. Proceed*. 26: 898–904, 1967

Ferrara J L M, Deeg H J: *New Engl. J. Med*., 324:10, 1991

Fisher C J, Slotman G J, Opal S M, et al.: *Circ. Shock*, 1: 42, 1993

Galanos C, Freudenberg M: *Immunobiology*, 187: 346, 1993

Gerard C, Bruyns C, Marchant A. et al: *J. Exp. Med*., 177: 547, 1993

Ghosh A K, Rakshit M M, Ghosh D K: *Indian J. Med Res*., 78, 407, 1983

Ghosh A K, Bhattacharyya A A, Ghosh D K: *Exp. Parasitol.*, 60, 404, 1985

Glauser M P, Hemann D, Baumgartner J D, Cohen J: *Clinical Infectious Diseases*, 18 (Suppl. 2): S205, 1994
Grebe S C, Streilein J W: *Adv. Immunol.*, 22:119, 1976
Greenman R L, Schein R M, Martin M A, et al.: *JAMA*, 266: 1097, 1991
Howard M, Muchameul T, Andrade S, Menon S: *J. Exp. Emed.*, 177:1205, 1993
Kametani et al. J. Chem Soc. (C) 2036, 1969.
Kendra J, Barrett A J, Lucas C: *Clin. Lab. Haematol.*, 3: 19, 1981
Kennedy M S, Deeg H J, Strob R, Doney K, Sullivan K M, Witherspoon R P, Applebaum F R, Stewart P, Sanders J, Buckner C D, Martin P, Weldon P, Thomas E D: *Am. J. Med.*, 78: 978, 1985
Kersey J, Ramsay N. Vallera D: In: *Recent Advances in Bone marrow Transplantation*, Ed. Gale RP, pp-283, Alan R Liss Inc., New York, 1983
Knudsen P J, Dinarello C A, Strom T B: *J. Immunol*, 139: 4129–4134, 1987
Krey A K, Hahn F E: *Science*, 7, 755, 1969
Lahnborg D, Hedstrom K G, Nord C E: *Eur. Sug. Res.*, 14:401, 1982
Lesslauer W., Tabuchi H., Gentz R., Brockhaus M., Schlaeger E. J., Grau G., Piguet P. F., Pointaire P., Vassali P., Loetscher H. Eur. J. Immunol. 21:2883–2886, 1991
Lynn W A, Golenbock D T: *Immunology Today*, 13: 271, 1992
Maiti M., Nandi R, Chaudhri, K. FEBS LETT. 142:280–284, 1982
Marra M N, Wilde C G, Grifith J E, Snable J L, Scott R W: *J. Immunol.*, 144: 662, 1990
Morris R E: *Transplant. Rev.*, 6: 39–87, 1992
Morris R E, Wang J: *Transplant. Proc.* 23: 493–506, 1991
Nadkarni A K: In: *Indian Materia Medica*, Vol. 1, Popular Book Depot, Bombay, pp. 188, 1954
Powels R L, Clink H M, Spence D: *Lancet*, 1: 327, 1980
Sado S: *J. Pharmacol. Soc.* (Japan) 67: 166, 1947
Schreiber S C: *Cell*, 70: 365–368, 1992
Shamma M: *Isoquinoloine Alkaloids*, Academic Press, New York, pp.308, 1972
Sainsbury et al. *Tetrahedron* 25, 1881, 1969
Sullivan K M: In: *Clinical Bone marrow Transplantation*, Eds. Blume K G, Petz L D, pp: 91, Chuchill Livingstone Inc., New York, 1983
Steck E A: *Prog Drug Res* 18, 289, 1974
Subbaiah T V, Amin A H: *Nature* 215, 527, 1967
Takeuchi T, Linuma H, Kunimoto S, Masuda T, Ishizuka M, Takeuchi M, Hamada M, Naganawa H, Kondo S, Umezava H: *J. Antibiotic* (Tokyo) 34: 1619–1621, 1981
Thomas E D, Strob R, Clift R A: *N. Engl. J. Med.*, 282:832, 1975
Turka L A, Dayton J. Sinclair G, Thompson C B, Mitchell B S: *J. Clin. Invest.*, 87: 940–948, 1991
Tutschka P. J., Beschomer W. E., Allison W. E., Burns W. H. Santos G. W. *Nature* 280:148–151, 1979
Umeda Y, Moriguchi M., Kuroda H, Nakamua T, Linuma H, Takeuchi T, Umezawa H: *J. Antibiotic* (Tokyo) 38: 886–898, 1985
Weiss J. Elsbach P, Shu C, et al.: *J. Clin. Invest.*, 90: 1122, 1992
Zanker B, Walz G. Weider K J., Strom T B: *Transplantation*, 49: 198–201, 1990
Ziegler E J, Fisher C J, Sprung C L et al., *N. Engl. J. Med.*, 324: 429, 1991

What is claimed is:

1. A method of treating TNF mediated or induced septic shock comprising suppressing TNF induced effects or inhibiting TNF-mediated effects by administering a therapeutically effective amount of berberine or a pharmaceutically acceptable salt thereof to a patient in need of such treatment.

2. The method according to claim 1 wherein the berberine or pharmaceutically acceptable salt thereof is administered topically, orally, by injection, transdermally, intravenously, intraarterially, intraperitoneally, intrapleurally, subcutaneously, intramuscularly, sublingually, intraepidermally or rectally.

3. The method according to claim 1 wherein the amount of berberine or pharmaceutically acceptable salts thereof administered on a daily basis is 1 to 20 mg/kg of body weight.

4. The method according to claim 1, wherein the patient is immunocompromised.

5. A method of preventing TNF mediated or induced septic shock comprising suppressing TNF induced effects or inhibiting TNF mediated effects by administering a therapeutically effective amount of berberine or a pharmaceutically acceptable salt thereof to a patient at risk for developing septic shock.

6. The method according to claim 5 wherein berberine or pharmaceutically acceptable salt thereof is administered to a host prior to transplantation of an organ or bone marrow.

7. The method according to claim 5 wherein berberine or pharmaceutically acceptable salt thereof is administered to a host following transplantation of an organ or bone marrow.

8. The method according to claim 5 wherein the berberine or pharmaceutically acceptable salt thereof is administered topically, orally, by injection, transdermally, intravenously, intraarterially, intraperitoneally, intrapleurally, subcutaneously, intramuscularly, sublingually, intraepidermally or rectally.

9. The method according to claim 5 wherein the amount of berberine or pharmaceutically acceptable salt thereof administered on a daily basis is 1 to 20 mg/kg of body weight.

10. The method according to claim 5 wherein the patient has suffered burns.

11. The method according to claim 5 wherein the berberine or pharmaceutically acceptable salt thereof is administered to the patient prior to the time the patient will undergo surgery.

12. The method according to claim 11 wherein the berberine or pharmaceutically acceptable salt thereof is administered topically, orally, by injection, transdermally, intravenously, intraarterially, intraperitoneally, intrapleurally, subcutaneously, intramuscularly, sublingually, intraepidermally or rectally.

13. The method according to claim 11 wherein the amount of berberine or pharmaceutically acceptable salt thereof administered on a daily basis is 1 to 20 mg/kg of body weight.

14. The method according to claim 11 wherein the berberine or pharmaceutically acceptable salt thereof is administered at least 24 hours before surgery.

15. The method according to claim 5, wherein the patient is immunocompromised.

16. A method of treating a TNF mediated or induced disease or symptoms or indications of the disease comprising suppressing TNF induced effects or inhibiting TNF-mediated effects by administering a therapeutically effective amount of berberine or a pharmaceutically acceptable salt thereof to a patient in need of such treatment.

17. The method according to claim 16, wherein the patient is immunocompromised.

18. The method according to claim 16, wherein the disease is an autoimmune disorder.

19. The method according to claim 16, wherein the disease is an allogenic or antigenic response.

20. A method of preventing a TNF mediated or induced disease comprising suppressing TNF induced effects or inhibiting TNF mediated effects by administering a therapeutically effective amount of berberine or a pharmaceutically acceptable salt thereof to a patient at risk for developing a TNF mediated or induced disease wherein the disease is graft vs. host disease, septic shock, or IL-2 or IFNy mediated autoimmune disorder.

21. The method according to claim 20, wherein the patient is immunocompromised.

* * * * *